US008150134B2

(12) United States Patent
Lee et al.

(10) Patent No.: US 8,150,134 B2
(45) Date of Patent: Apr. 3, 2012

(54) METHOD FOR ENHANCING BLOOD VESSELS IN ANGIOGRAPHY IMAGES

(75) Inventors: Sungyoung Lee, Seongnam-si (KR); Tae-Seong Kim, Suwon-Si (KR); Young-Koo Lee, Yongin-si (KR); Phan Tran Ho Truc, Yongin-si (KR)

(73) Assignee: Industry-Academic Cooperation Foundation of Kyung Hee University, Yongin-si (KR)

( * ) Notice: Subject to any disclaimer, the term of this patent is extended or adjusted under 35 U.S.C. 154(b) by 1049 days.

(21) Appl. No.: 11/892,030

(22) Filed: Aug. 17, 2007

(65) Prior Publication Data
US 2009/0046910 A1 Feb. 19, 2009

(51) Int. Cl.
*G06K 9/36* (2006.01)
*G06K 9/40* (2006.01)

(52) U.S. Cl. ........ 382/132; 382/130; 382/254; 382/260; 382/263

(58) Field of Classification Search .................. 382/131, 382/132, 130, 254, 260–265
See application file for complete search history.

(56) References Cited

OTHER PUBLICATIONS

M. Asmatullah Khan et al., "A Decimation Free Directional Filter Banks for Medical Image Enhancement," Information Technology Journal 3 (2), pp. 146-149, 2004.*
Mohammad A. U. Khan et al., "Coronary Angiogram Image Enhancement Using Decimation-Free Directional Filter Bank," IEEE International Conference on Acoustic, Speech, and Signal Processing 2004, vol. 5, pp. 441-444, 2004.*
Mohammad A. U. Khan et al., "Comparative Analysis of Decimation-Free Directional Filter Bank With Directional Filter Bank: in Context of Image Enhancement," 9th International Multitopic Conference, IEEE INMIC 2005, pp. 1-8, Dec. 24-25, 2005.*
Truong T. Nguyen et al., "Efficient Implementation of Undecimated Directional Filter Banks," 14th European Signal Processing Conference (EUSIPCO 2006), Florence, Italy, Sep. 4-8, 2006.*
Mohammad A. U. Khan et al., "Vessel Enhancement Using Directional Features," Information Technology Journal 6 (6), pp. 851-857, 2007.*
Phan Tran Ho Truc et al., "A New Approach to Vessel Enhancement in Angiography Images," IEEE/ICME International Conference on Complex Medical Engineering 2007, pp. 878-884, May 23-27, 2007.*
Phan Tran Ho Truc et al., "Vessel Enhancement in Angiography Images using Decimation-free Directional Filter Bank," Proceedings of the 2007 International Conference on Image Processing, Computer Vision, Pattern Recognition, IPCV 2007, Las Vegas, Nevada, Jun. 25-28, 2007.*
Phan T. H. Truc et al., "Vessel enhancement filter using directional filter bank," Computer Vision and Image Understanding 113, pp. 101-112, 2009.*
A. Frangi et al.: "Multiscale vessel enhancement filtering," Proc. Int. Conf. Medical Image Computing Computer-Assisted Assisted Intervention, LNCS, vol. 1496, pp. 130-137, 1998.
H. Shikata et al: "Automated segmentation of pulmonary vascular tree from 3D CT images," Proc. SPIE Int. Symp. Medical Imaging, San Diego, CA, 10 pages, 2004.
R. Bamberger et al. "A filter bank for the directional decomposition of images: theory and design," IEEE trans. Sig. Proc., vol. 40, No. 4, pp. 882-893, 1992.

* cited by examiner

*Primary Examiner* — Allen C. Ho
(74) *Attorney, Agent, or Firm* — Rothwell, Figg, Ernst & Manbeck, P.C.

(57) ABSTRACT

Disclosed is a method for enhancing blood vessels in angiography images. The method incorporates the use of linear directional features present in an image, extracted by a Directional Filter Bank, to obtain more precise Hessian analysis in noisy environment and thus can correctly reveal small and thin vessels. Also, the directional image decomposition helps to avoid junction suppression, which in turn, yields continuous vessel tree.

8 Claims, 23 Drawing Sheets

METHOD FOR ENHANCING BLOOD VESSELS IN ANGIOGRAPHY IMAGES

BACKGROUND

1. Technical Field

The invention generally concerns enhancement filtering to improve visibility of blood vessels and more practically to a framework for vessel enhancement filtering in angiography images.

2. Description of the Related Art

The common way to interpret vasculature images, e.g. the Magnetic Resonance Angiography (MRA) images, is to display them in Maximum Intensity Projection (MIP) in which the stack of slices is collapsed into a single image for viewing. MIP is performed by assigning to each pixel in the projection the brightest pixel over all slices in the stack. With this type of display, small vessels with low contrast are hardly visible and other organs may be projected over the arteries. FIG. 1 may demonstrate that small vessels tend to resemble background. A vessel enhancement procedure as a pre-processing step for maximum intensity projection display will help to diminish these two limitations.

There are a variety of vessel enhancement methods in literature. The simplest one is to threshold the raw data but this makes the segmentation process incorrectly label bright noise regions as vessels and cannot recover small vessels which may not appear connected in the image. Recently, Hessian-based approaches have been utilized in numerous vessel enhancement filters. These filters are based on the principal curvatures, which are determined by the Hessian eigenvalues, to differentiate the line-like (vessel) from the blob-like (background) structures. However, their disadvantage is that they are highly sensitive to noise due to second-order derivatives. Moreover, they tend to suppress junctions which are characterized same as the blob-like structures using the principal curvature analysis. Junction suppression in turn leads to discontinuity of the vessel network.

SUMMARY

The present invention has been made to solve the above problems occurring in the prior art. There is provided a method for the vessel enhancement filter utilizing the linear directional information present in an image. The method comprises decomposing the input angiography image into directional images $T_i$ using Decimation-free Directional Filter Bank (DDFB), removing non-uniform illumination by employing n distinct homomorphic filters matched with its corresponding directional image, enhancing vessels in every directional image, and re-combining all enhanced directional images. Further consistent with the present invention, wherein said DDFB comprises filtering the input angiography image with $H_{00}(\omega_1, \omega_2)$ and $H_{11}(\omega_1, \omega_2)$ hourglass-shaped like passbands, filtering with $H_{00}(Q^T(\omega_1, \omega_2))$ and $H_{11}(Q^T(\omega_1, \omega_2))$, where T represents transpose and Q is Quincunx downsampling matrix, and filtering with $H_{00}(R_i Q^T Q^T(\omega_1, \omega_2))$ and $H_{11}(R_i Q^T Q^T(\omega_1, \omega_2))$ where $R_i$ (i=1, 2, 3, and 4) are resampling matrices.

$$Q = \begin{pmatrix} 1 & 1 \\ -1 & 1 \end{pmatrix}$$

$$R_1 = \begin{pmatrix} 1 & 1 \\ 0 & 1 \end{pmatrix}$$

$$R_2 = \begin{pmatrix} 1 & -1 \\ 0 & 1 \end{pmatrix}$$

$$R_3 = \begin{pmatrix} 1 & 0 \\ 1 & 1 \end{pmatrix}$$

$$R_4 = \begin{pmatrix} 1 & 0 \\ -1 & 1 \end{pmatrix}$$

Output of the vessel enhancement filter for one directional image is $$\Phi(p) = \max_{\sigma \in S} \phi_\sigma(p),$$

where p is coordinate (x',y'), S is a range, and $\sigma$ is a various scale. The coordinates Ox'y' is obtained by rotating Oxy by the angle associated with that directional image. $\phi_o(p)$ is based on the diagonal values of the Hessian matrix H' in the coordinates Ox'y'.

$$H' = \begin{bmatrix} \frac{\partial^2 I_i}{\partial x'^2} & \frac{\partial^2 I_i}{\partial x' \partial y'} \\ \frac{\partial^2 I_i}{\partial x' \partial y'} & \frac{\partial^2 I_i}{\partial y'^2} \end{bmatrix}$$

where $$\frac{\partial^2 I_i}{\partial x'^2} = \frac{\partial^2 I_i}{\partial x^2}\cos^2\theta_i + \frac{\partial^2 I_i}{\partial x \partial y}\sin(2\theta_i) + \frac{\partial^2 I_i}{\partial y^2}\sin^2\theta_i,$$

$$\frac{\partial^2 I_i}{\partial y'^2} = \frac{\partial^2 I_i}{\partial x^2}\cos^2\theta_i - \frac{\partial^2 I_i}{\partial x \partial y}\sin(2\theta_i) + \frac{\partial^2 I_i}{\partial y^2}\cos^2\theta_i,$$

$$\frac{\partial^2 I_i}{\partial x' \partial y'} = -\frac{1}{2}\frac{\partial^2 I_i}{\partial x^2}\sin(2\theta_i) + \frac{\partial^2 I_i}{\partial x \partial y}\cos(2\theta_i) + \frac{1}{2}\frac{\partial^2 I_i}{\partial y^2}\sin(2\theta_i)$$

Specifically, the input image is first decomposed by DDFB into a set of directional images, each of which contains linear features in a narrow directional range. The directional decomposition has two advantages. One is, noise in each directional image will be significantly reduced compared to that in the original one due to its omni-directional nature. The other is, because one directional image contains only vessels with similar directions, the principal curvature calculation in it is facilitated. Then, distinct appropriate enhancement filters are applied to enhance vessels in the respective directional images. Finally, the enhanced directional images are re-combined to generate the output image with enhanced vessels and suppressed noise. This decomposition-filtering-recombination scheme also helps to preserve junctions.

DETAILED DESCRIPTION

Embodiment 1

Figure 1:
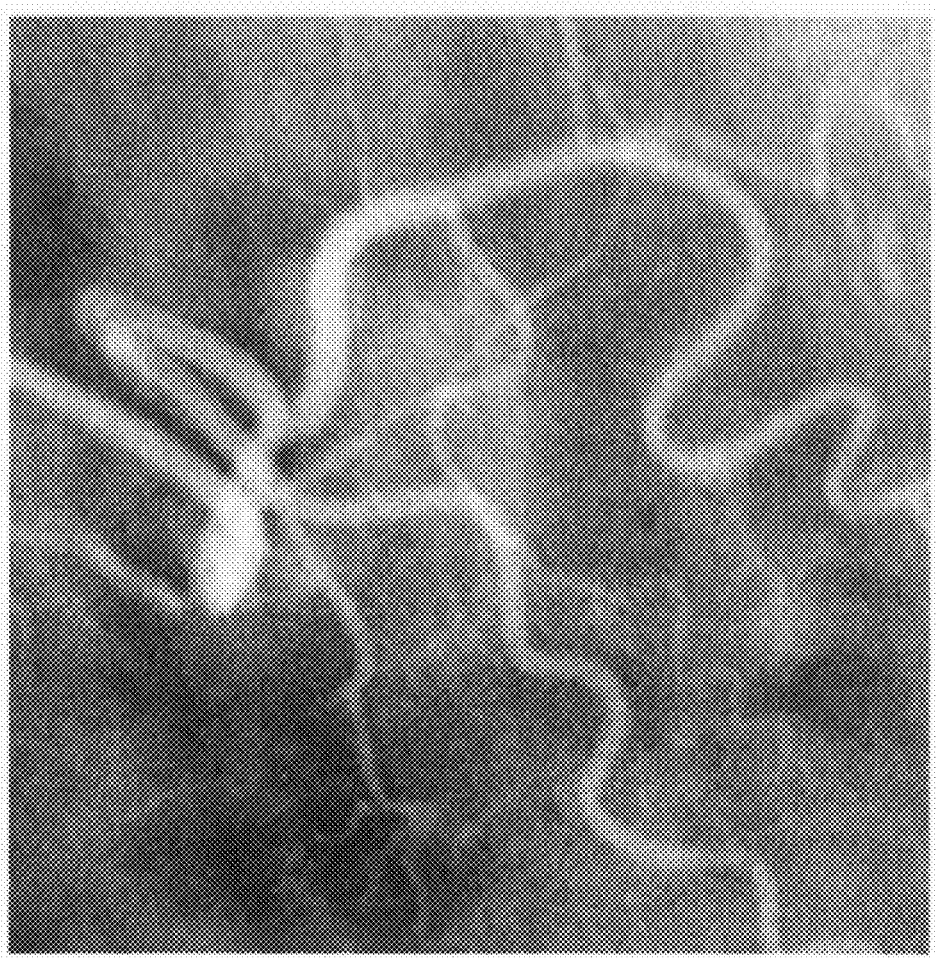
FIG. 1 is showing an angiography image with small vessels.

Whereinafter, a embodiment consistent with the present invention will be described with reference to the drawing.

Figure 2:
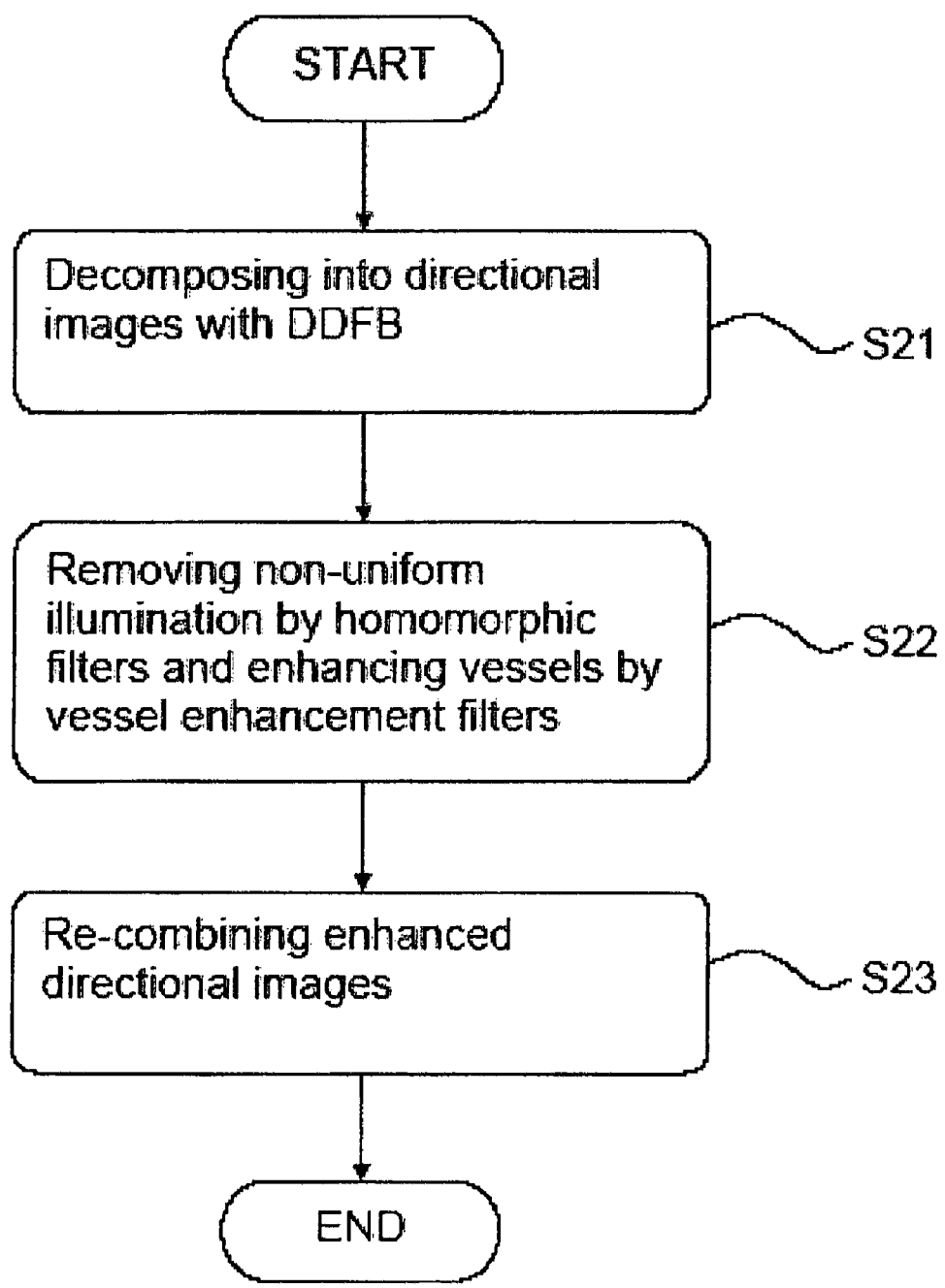
FIG. 2 is flowchart showing a method of enhancing blood vessels consistent with the present invention.

The proposed method consists of three steps, as shown in FIG. 2: First step (step 21) is construction of directional images by decomposing input image, second step (step 22) is vessel enhancement, and third step (step 23) is recombination of enhanced directional images.

As shown in FIG. 2, the decomposing with DDFB (step 21), which is the first step of decomposing input angiography image into directional images. Next, removing non-uniform illumination by homomorphic filter and enhancing directional images by appropriate enhancement filters (step 22), which is the second step of enhancement filtering to improve visibility of blood vessels. Thereafter, re-combining directional images (step 23), which is the third step of re-combining all enhanced directional images.

So, the invention is characterized as follows.

To enhance vessels in angiography images, input vessel image is decomposed to a set of directional images using DDFB. The non-uniform illumination is removed by employing a homomorphic filter matched with its corresponding directional image. The filtering process is based on the Hessian eigenvalues and filtering process is applied on the set of directional images.

Directional Filter Bank (DFB) can decompose the spectral region of an input image into $n=2^k$ ($k=1, 2, \ldots$) wedge-shaped like subbands which correspond to linear features in a specific direction in spatial domain.

One disadvantage of DFB is that the subbands are smaller in size as compare to the size of input image. The reduction in size is due to the presence of decimators. As far as image compression is concerned, decimation is a must condition. However, when DFB is employed for image analysis purposes, decimation causes two problems. One is, as we increase the directional resolution, spatial resolution starts to decrease, due to which we loose the correspondence among the pixels of DFB outputs. The other is, an extra process of interpolation is involved prior to enhancement implementation. This extra interpolation process not only affects the efficiency of whole system but also produces false artifacts which can be harmful especially in case of medical imagery. Some vessels may be broken and some can be falsely connected to some other vessels due to the artifacts produced by interpolation. So a need arises to modify directional filter bank structure in a sense that no decimation is required during analysis section. We suggest to shift the decimators and resamplers to the right of the filters to create the DDFB, which yields directional images rather than directional subbands. This consequently results in elimination of interpolation and naturally fits the purposes of feature analysis.

The decomposing step (step 21) of applying DDFB comprise as following stages. First stage of filtering the input angiography image with $H_{00}(\omega_1, \omega_2)$ and $H_{11}(\omega_1, \omega_2)$ hour-glass-shaped like passbands, Second stage of filtering with $H_{00}(Q^T(\omega_1, \omega_2))$ and $H_{11}(Q^T(\omega_1, \omega_2))$, where T represents transpose and Q is Quincunx downsampling matrix, and Third stage of filtering with $H_{00}(R_i Q^T Q^T(\omega_1, \omega_2))$ and $H_{11}(R_i Q^T Q^T(\omega_1, \omega_2))$.

Figure 3A:
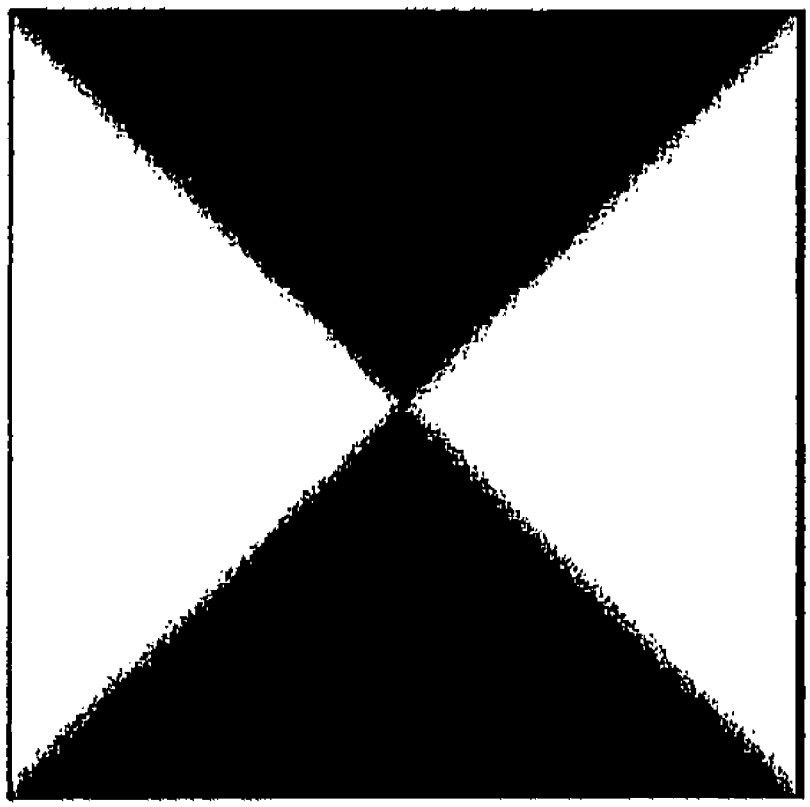
FIGS. 3A and 3B are showing the frequency responses of hourglass-shaped like filters.
Figure 3B:
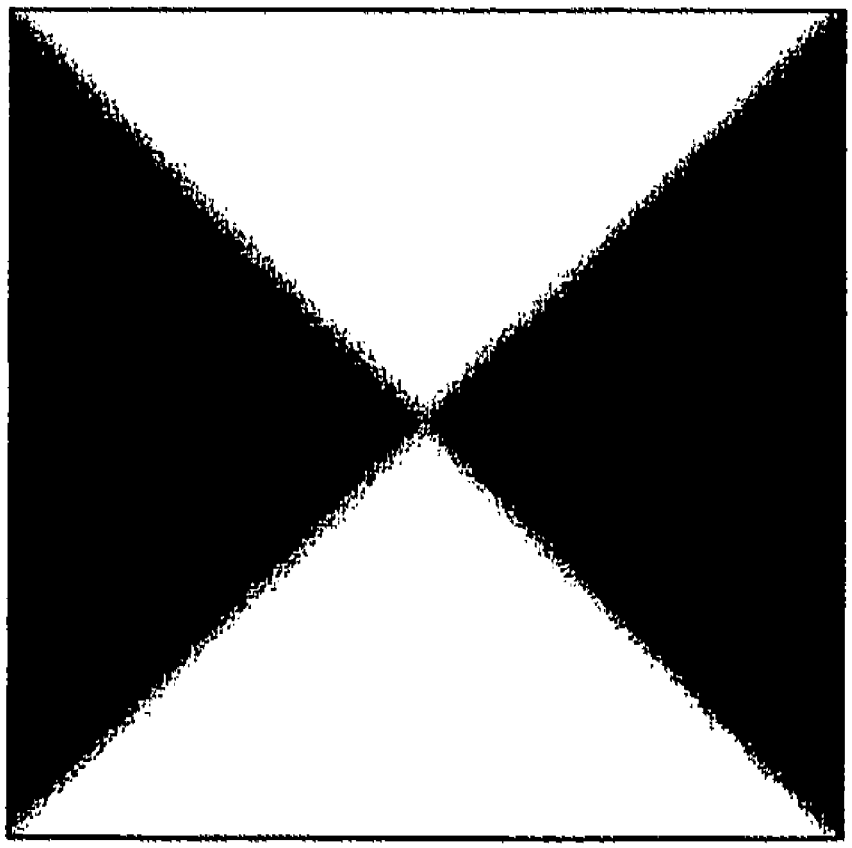
Figure 4A:
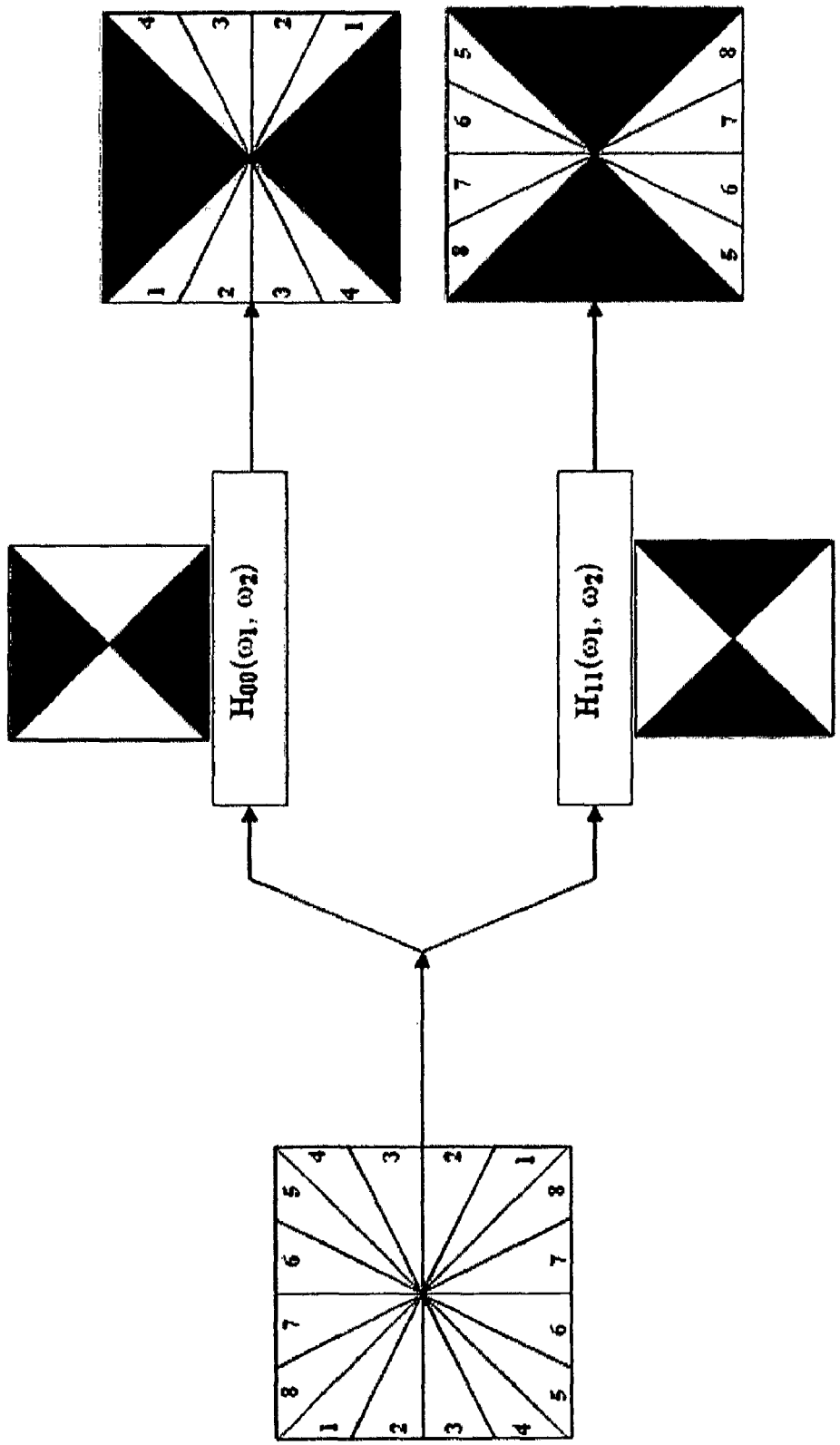
FIG. 4A is showing the First stage of DDFB structure.

At first the stage of applying DDFB, construction of first stage of DDFB only requires two filters. Filters at first stage of DDFB are $H_{00}(\omega_1, \omega_2)$ and $H_{11}(\omega_1, \omega_2)$. They have hour-glass-shaped like passbands as shown in FIGS. 3A and 3B. FIG. 4A shows the block diagram of the first stage of DDFB.

At second the stage of applying DDFB, the filters required for construction of second stage are $H_{00}(Q^T(\omega_1, \omega_2))$ and $H_{11}(Q^T(\omega_1, \omega_2))$, where T represents transpose and Q is the Quincunx downsampling matrix.

$$Q = \begin{pmatrix} 1 & 1 \\ -1 & 1 \end{pmatrix} \qquad \text{–EQUATION 1–}$$

Figure 4B:
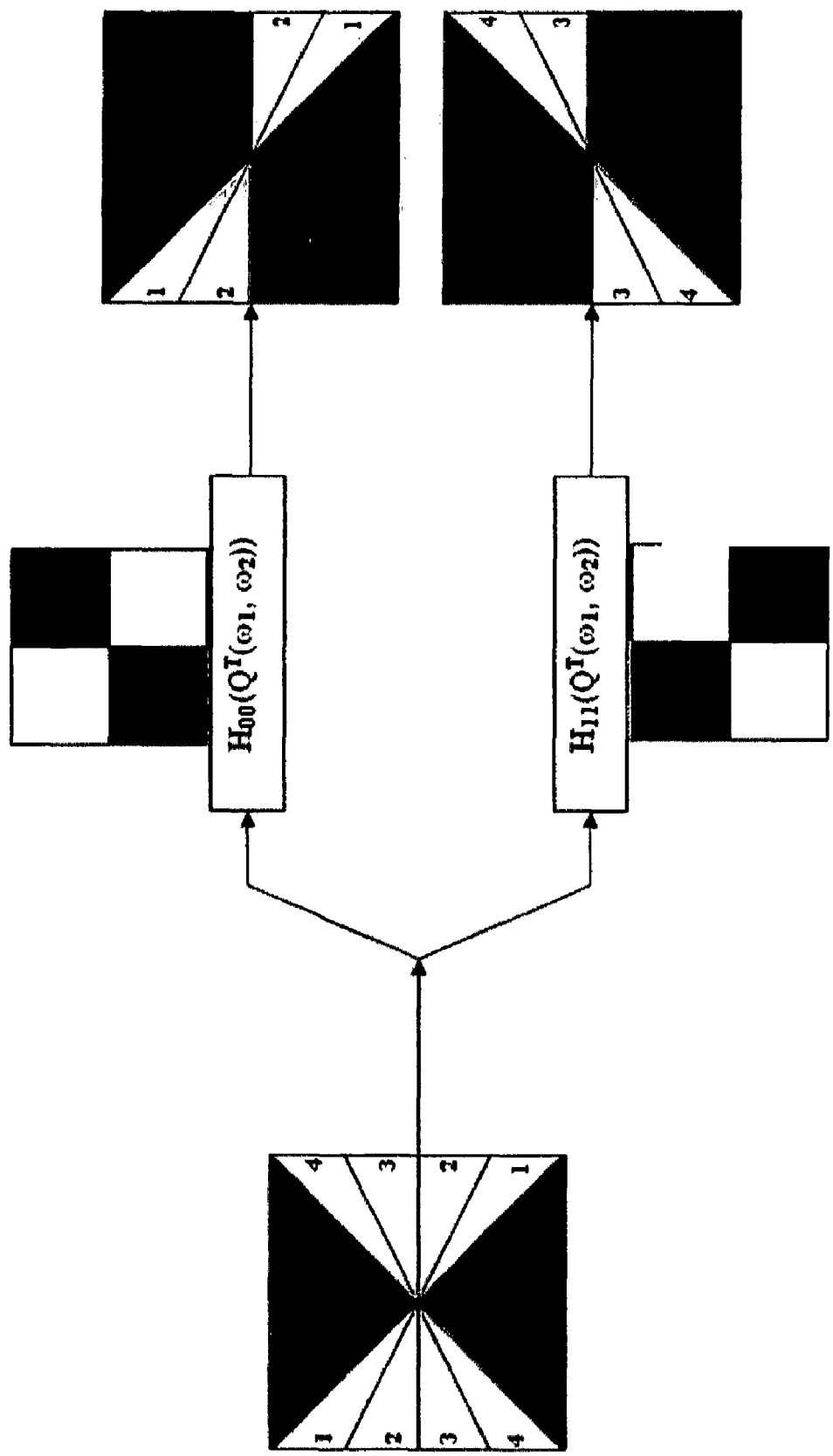
FIG. 4B is showing the Second stage of DDFB structure.

Spectral regions of directional images obtained after filtering through second stage filter are shown in FIG. 4B.

Figure 4C:
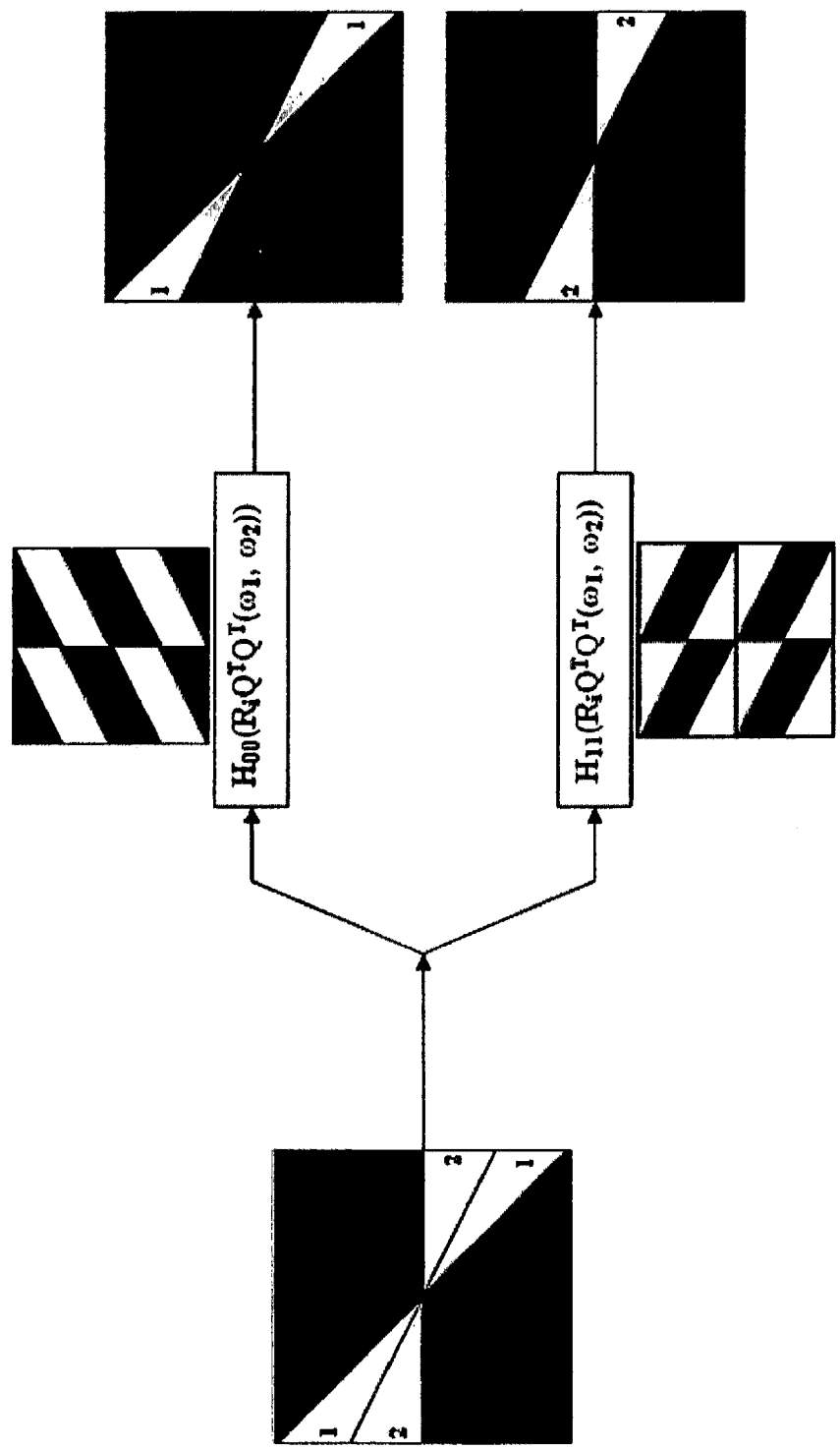
FIG. 4C is showing the Third stage of DDFB structure.

At third the stage of applying DDFB, filters used during the third stage of DDFB are $H_{00}(R_i Q^T Q^T(\omega_1, \omega_2))$ and $H_{11}(R_i Q^T Q^T(\omega_1, \omega_2))$, as shown in FIG. 4C where $R_i$ ($i=1, 2, 3,$ and 4) are resampling matrices.

$$\begin{aligned} R_1 &= \begin{pmatrix} 1 & 1 \\ 0 & 1 \end{pmatrix} \\ R_2 &= \begin{pmatrix} 1 & -1 \\ 0 & 1 \end{pmatrix} \\ R_3 &= \begin{pmatrix} 1 & 0 \\ 1 & 1 \end{pmatrix} \\ R_4 &= \begin{pmatrix} 1 & 0 \\ -1 & 1 \end{pmatrix} \end{aligned} \qquad \text{-EQUATION 2-}$$

Overall eight different filters are created to be used during the third stage.

By using the DDFB, the input image is decomposed to $n=2^k$ ($k=1, 2, \ldots$) directional images $T_i$. The motivation here is to detect thin and low-contrast vessels (which are largely directional in nature) while avoiding false detection of non-vascular structures. Directional segregation property of DDFB is helpful in eliminating randomly oriented noise patterns and non-vascular structures which normally yield similar amplitudes in all directional images (see FIGS. 6A to 6H).

Figure 5:
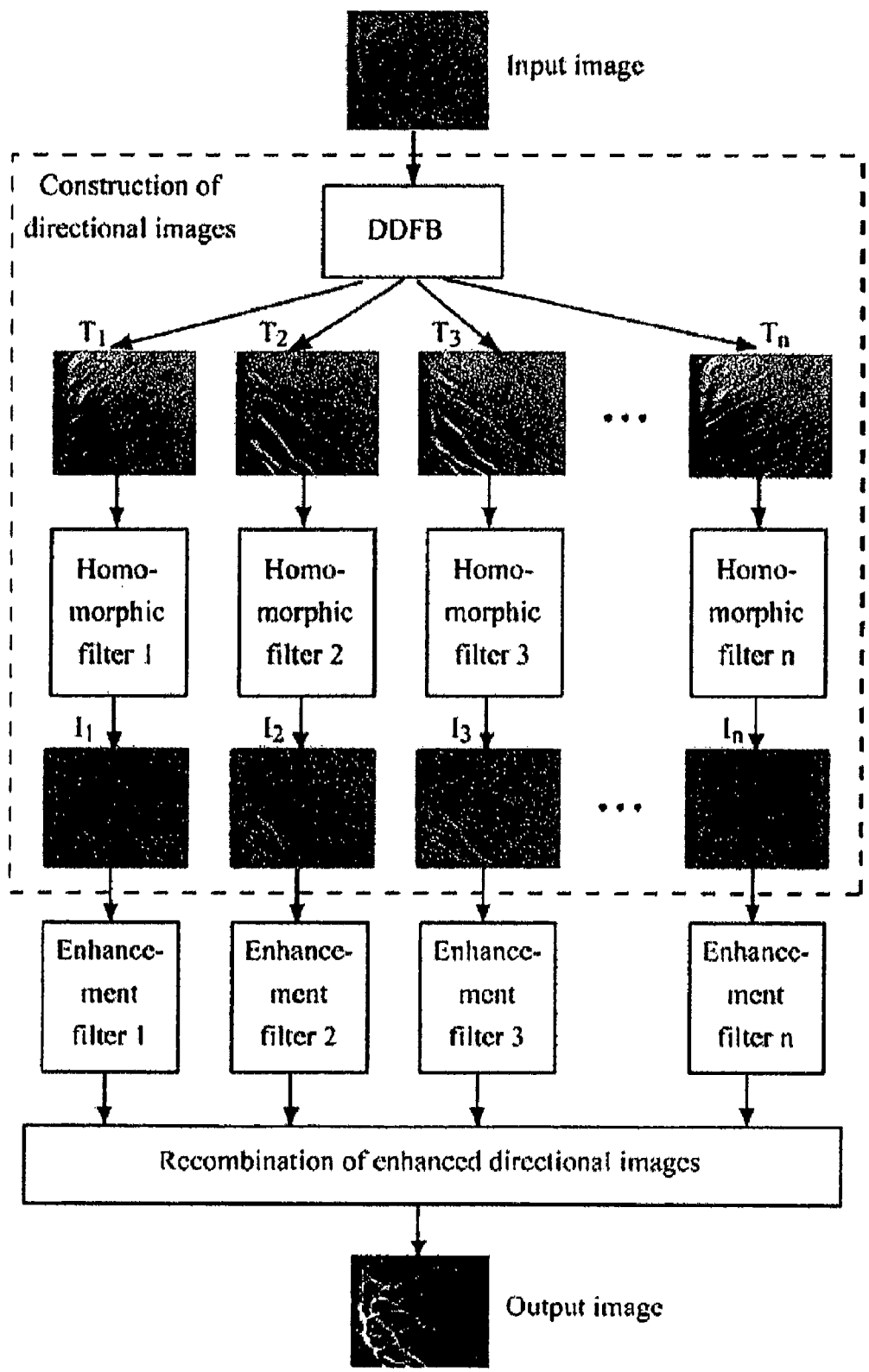
FIG. 5 is showing the block diagram of the present invention.
Figure 6A:
FIGS. 6A, 6B, 6C, 6D, 6E, 6F, 6G, and 6H are showing eight demonstrative directional images.
Figure 6B:
Figure 6C:
Figure 6D:
Figure 6E:
Figure 6F:
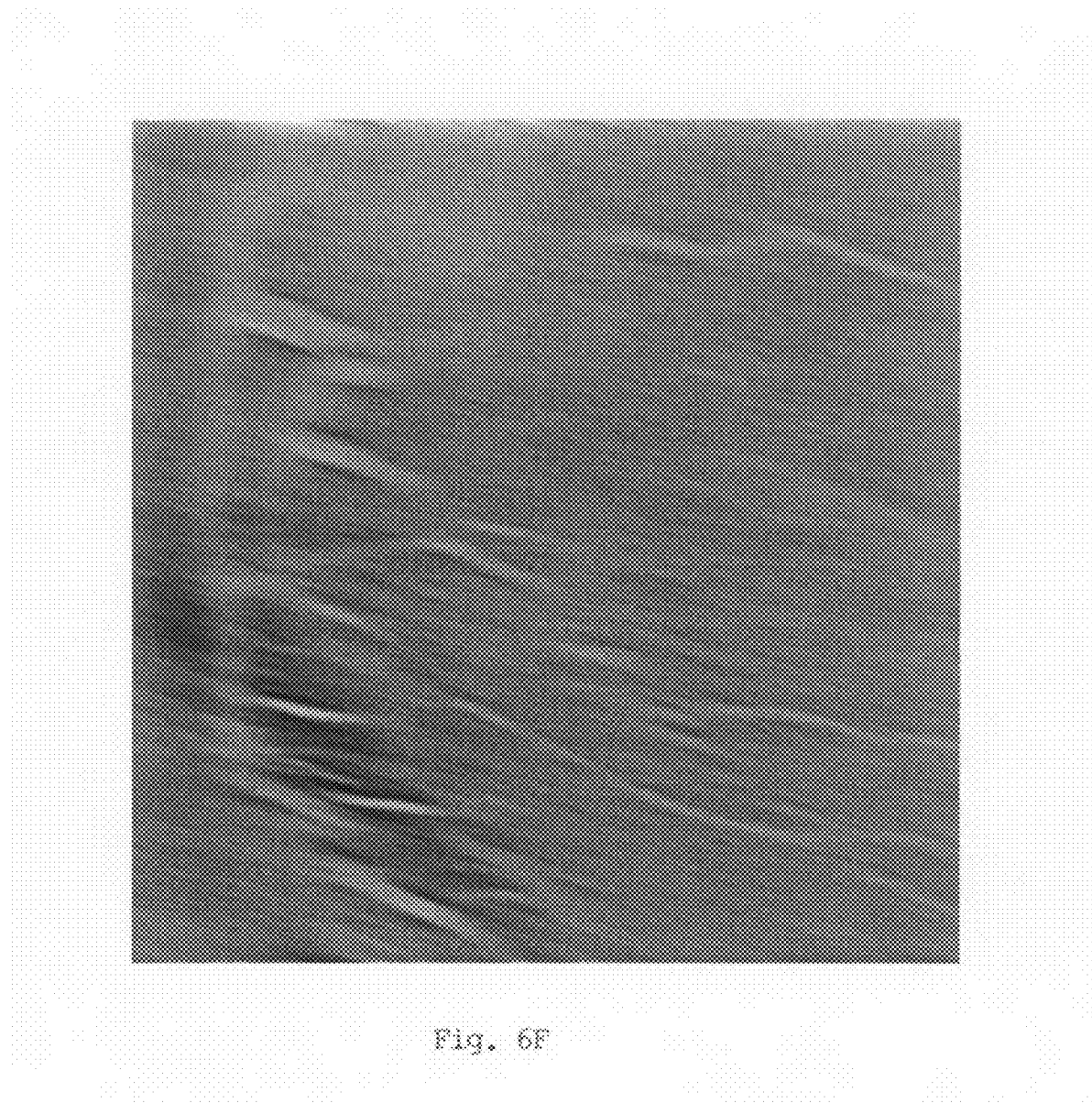
Figure 6G:
Figure 6H:
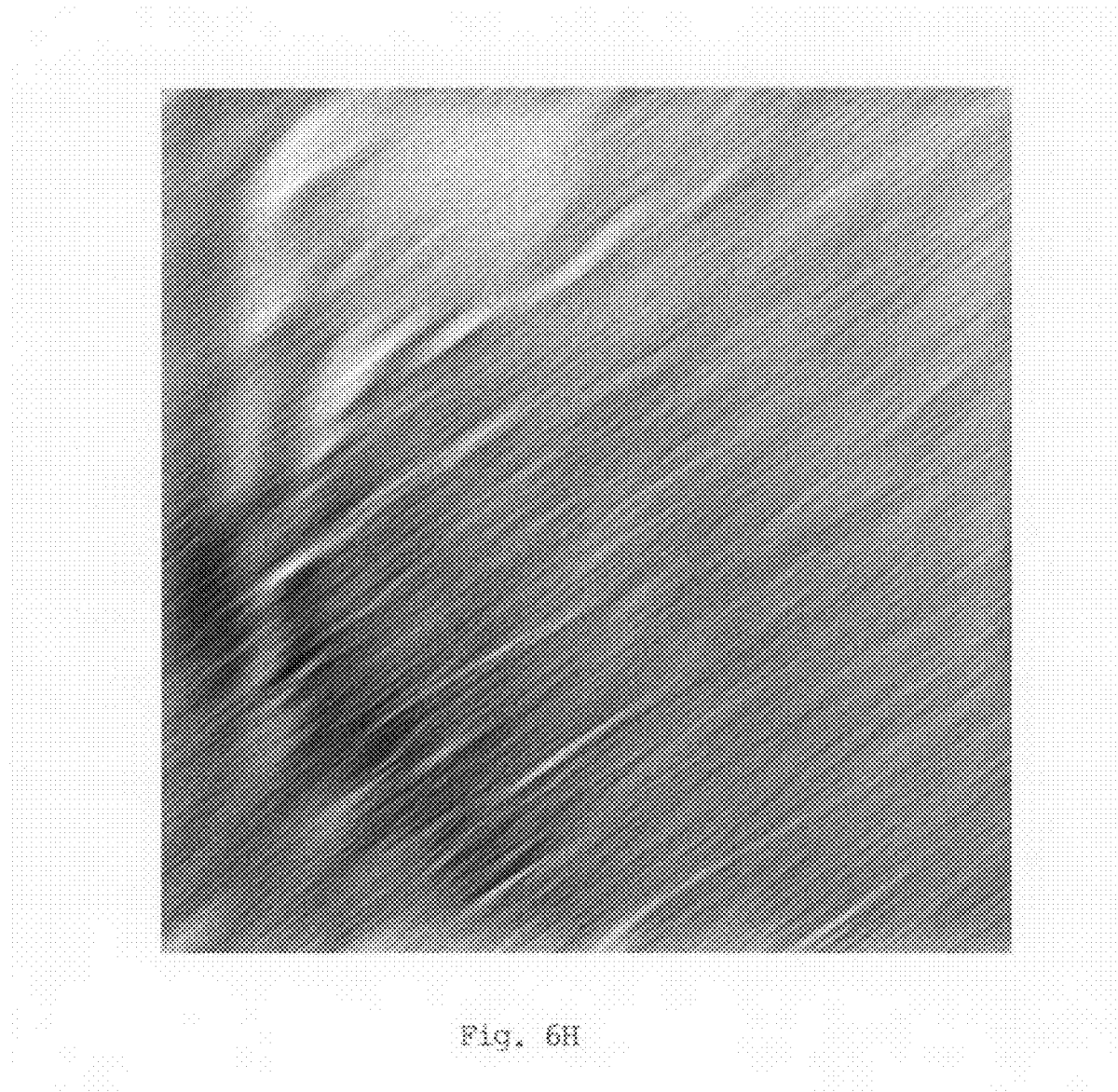
Figure 7A:
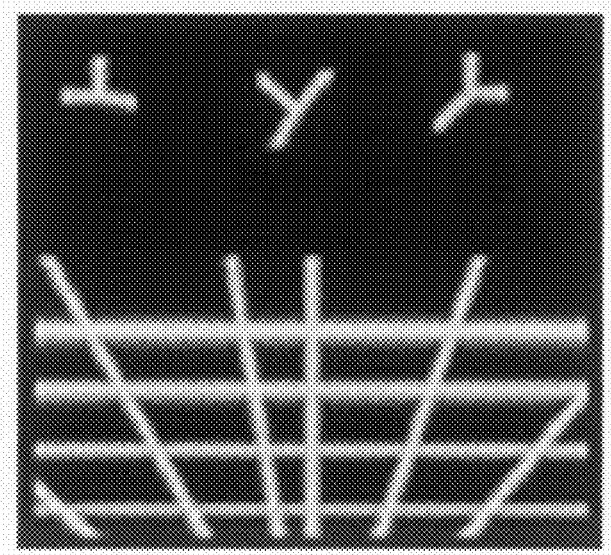
FIG. 7A is showing a synthetic image used to evaluating the performance of the present invention.
Figure 7B:
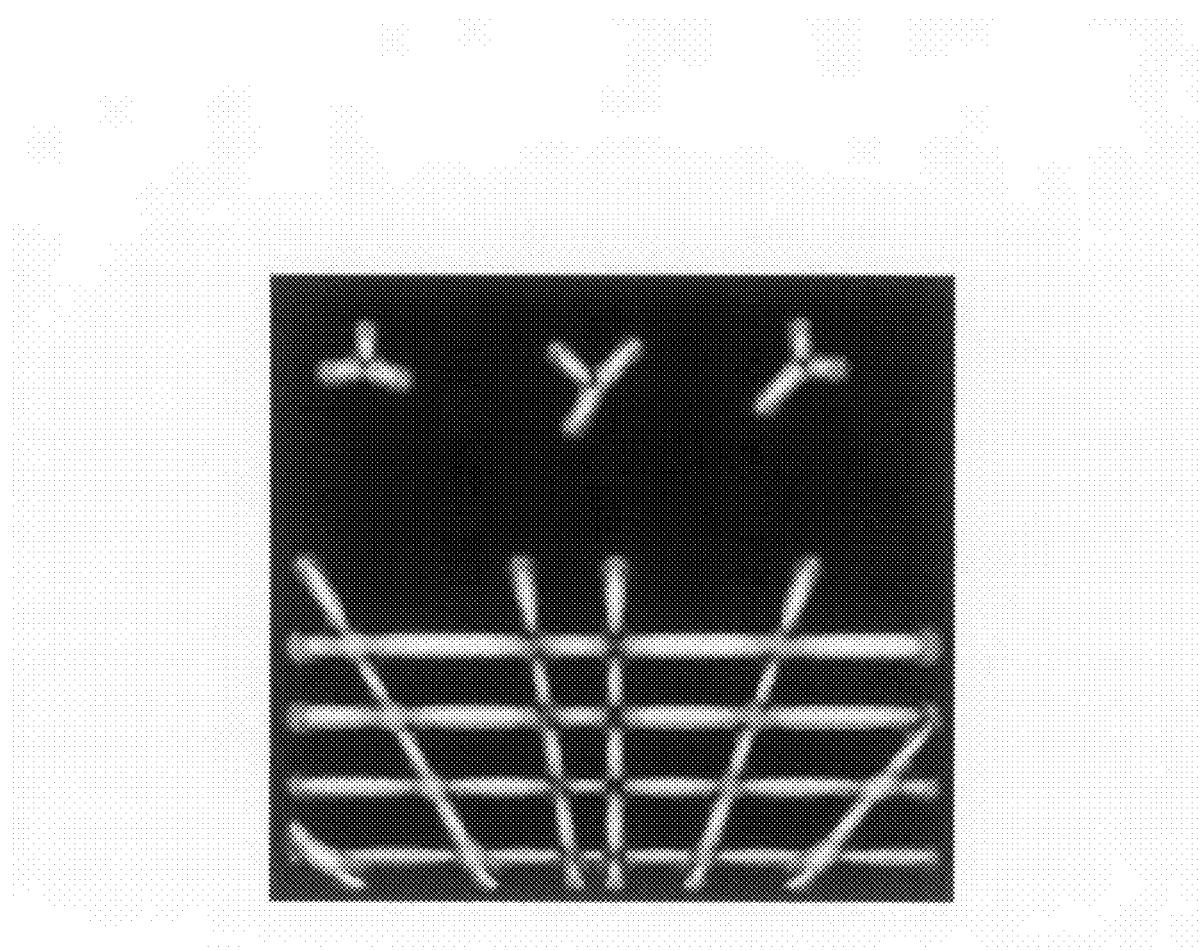
FIGS. 7B, 7C, and 7D are showing enhancement results of the Frangi filter, the Shikata filter and the present invention for the input image shown in FIG. 7A.
Figure 7C:
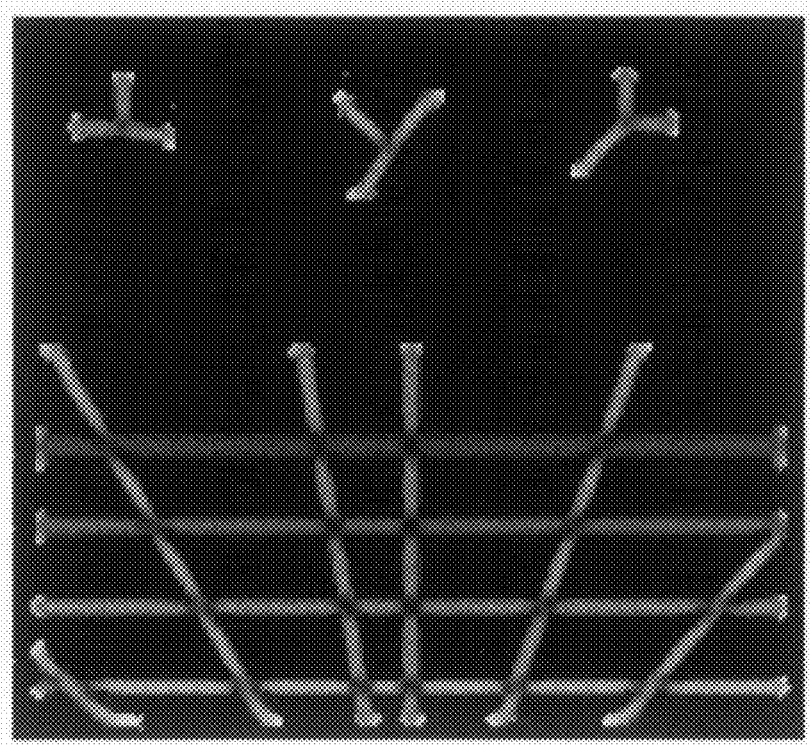
Figure 7D:
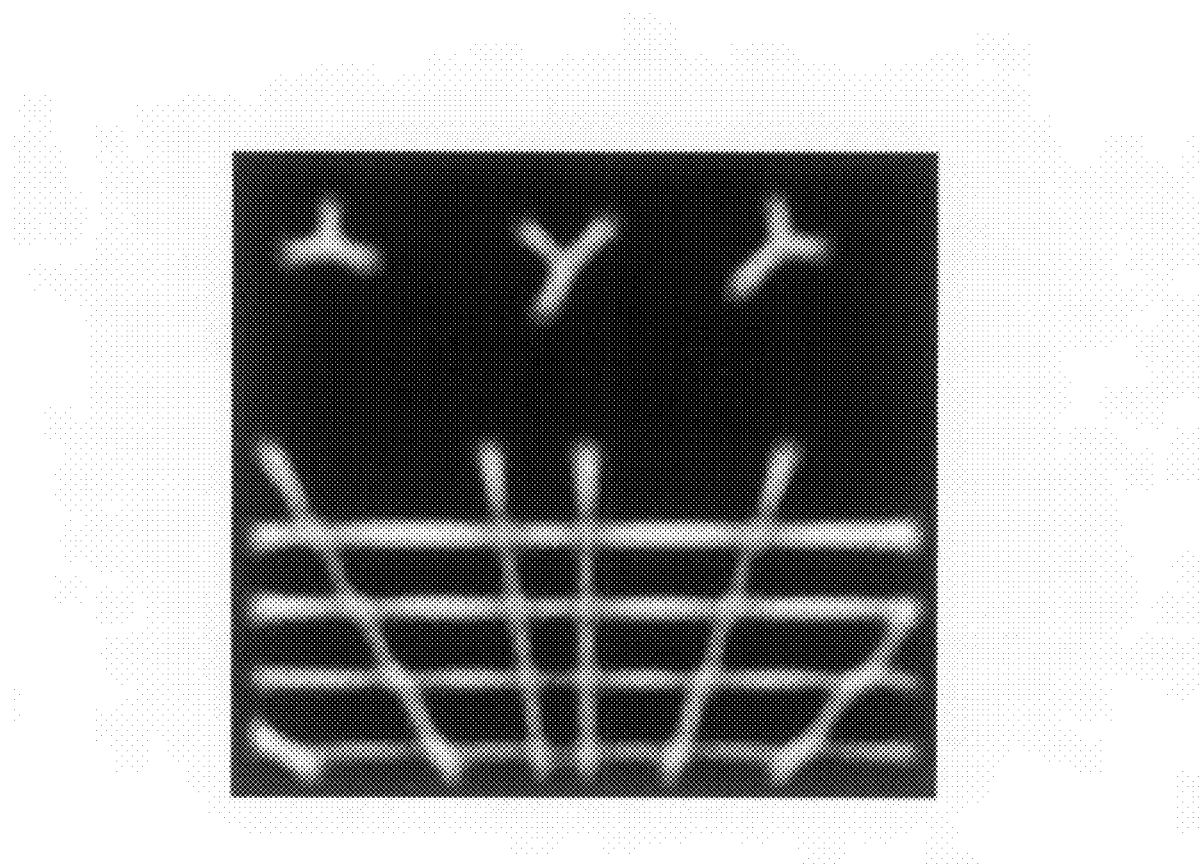

Before these directional images are enhanced in the next step, they are utilized to efficiently remove non-uniform illumination (NUI), which limits the correct vessel enhancement. One conventional approach to correct NUI is to directly apply homomorphic filtering on the original image. A general image can be characterized by two components: (1) the illumination component, which changes slowly in a neighborhood due to light source characteristics and thus is low-frequency, and (2) the reflectance component, which is determined by the amount of light reflected by the objects and therefore is high-frequency. The homomorphic filter is to suppress the low-frequency component while enhance the high-frequency one. However, the direct application of homomorphic filtering is sometimes unsatisfactory because it may enhance background noise which is normally high-frequency. Tuning the filter parameters in this case suffers from a compromise. The more NUI is removed, the more background noise is enhanced. Differently, we propose employing a homomorphic filter matched with its corresponding directional image as shown in the dash-boundary box in FIG. 5. This new arrangement provides us a better control on the parameters of individual homomorphic filter.

Explaining the second step (step 22) of vessel enhancement, we propose removing non-uniform illumination by homomorphic filter.

In order to compute the principal curvatures with less noise sensitiveness, it is necessary to align the vessel direction with the x-axis. One possible way is to rotate the directional images. Nevertheless, image rotation requires interpolation which is likely to create artifacts and thus is harmful especially in case of medical imagery. We therefore rotate the coordinates rather than the directional images.

Suppose the directional image $I_i$ (i=1 ... n) corresponds to the orientations ranging from $\theta_{i,min}$ to $\theta_{i,max}$ (counterclockwise angle). Its associated coordinates Oxy will be rotated to Ox'y' by an amount as large as the mean value $\theta_i$.

$$\theta_i = \frac{\theta_{i,\min} + \theta_{i,\max}}{2} \qquad \text{-EQUATION 3-}$$

Hessian matrix of the directional image $I_i$ in the new coordinates Ox'y' is determined as followed EQUATION 4.

$$H' = \begin{bmatrix} \frac{\partial^2 I_i}{\partial x'^2} & \frac{\partial^2 I_i}{\partial x' \partial y'} \\ \frac{\partial^2 I_i}{\partial x' \partial y'} & \frac{\partial^2 I_i}{\partial y'^2} \end{bmatrix} \qquad \text{-EQUATION 4-}$$

where $$\frac{\partial^2 I_i}{\partial x'^2} = \frac{\partial^2 I_i}{\partial x^2}\cos^2\theta_i + \frac{\partial^2 I_i}{\partial x \partial y}\sin(2\theta_i) + \frac{\partial^2 I_i}{\partial y^2}\sin^2\theta_i,$$

$$\frac{\partial^2 I_i}{\partial y'^2} = \frac{\partial^2 I_i}{\partial x^2}\sin^2\theta_i - \frac{\partial^2 I_i}{\partial x \partial y}\sin(2\theta_i) + \frac{\partial^2 I_i}{\partial y^2}\cos^2\theta_i,$$

$$\frac{\partial^2 I_i}{\partial x' \partial y'} = -\frac{1}{2}\frac{\partial^2 I_i}{\partial x^2}\sin(2\theta_i) + \frac{\partial^2 I_i}{\partial x \partial y}\cos(2\theta_i) + \frac{1}{2}\frac{\partial^2 I_i}{\partial y^2}\sin(2\theta_i)$$

The principal curvatures are then defined by the diagonal values of H'. These values are EQUATION 5.

$$PC_1 = 0; \qquad \text{-EQUATION 5-}$$
$$PC_2 = \frac{y'^2 - (\sigma_0^2 + \sigma^2)}{(\sigma_0^2 + \sigma^2)^2} I_i(x', y')$$

where σ selected in a range S is the standard deviation of the Gaussian kernel used in the multiscale analysis.

Practically, the vessel axis is not, in general, identical to the x'-axis and so $PC_1 \approx 0$.

Inside the vessel, $|y'| < \sqrt{\sigma_0^2 + \sigma^2}$ and thus $PC_2$ is negative. Therefore, vessel pixels are declared when $PC_2 < 0$ and $$\left|\frac{PC_1}{PC_2}\right| \ll 1.$$

To distinguish background pixels from others, we define a structureness measurement as EQUATION 6.

$$C = \sqrt{PC_1^2 + PC_2^2} \qquad \text{EQUATION 6}$$

This structureness C should be low for background which has no structure and small derivative magnitude.

Based on the above observations, the vessel filter output can be defined as EQUATION 7.

$$\phi_\sigma(p) = \eta(PC_2)\exp\left(-\frac{R^2}{2\beta^2}\right)\left[1 - \exp\left(-\frac{C^2}{2\gamma^2}\right)\right], \qquad \text{-EQUATION 7-}$$

where p=(x',y'), R=$PC_1/PC_2$, β and γ are adjusting constants, and $$\eta(z) = \begin{cases} 0 & \text{if } z \geq 0; \\ 1 & \text{if } z < 0. \end{cases}$$

The filter is analyzed at different scales σ in a range S. When the scale matches the size of the vessel, the filter response will be maximum. Therefore, the final vessel filter response is EQUATION 8.

$$\Phi(p) = \max_{\sigma \in S} \phi_\sigma(p) \qquad \text{-EQUATION 8-}$$

One filter (EQUATION 8) is applied to one directional image to enhance vessel structures in it.

Explaining the third step (step 23) of re-combining directional images, each directional image now contains enhanced vessels in its directional range and is called the enhanced directional image.

Denote $\Phi_i(p)$, i=1 ... n, as the enhanced directional images. Another advantage of DDFB is that its synthesis is achieved by simply summing all directional images. Thus, the output enhanced image F(p) can be obtained by EQUATION 9.

$$F(p) = \frac{1}{n}\sum_{i=1}^{n} \Phi_i(p) \qquad \text{-EQUATION 9-}$$

The whole filtering procedures can be summarized as follows. First, the input angiography image is decomposed into n=$2^k$ (k=1, 2, ...) directional images $T_i$ using DDFB. Then, n distinct homomorphic filters are employed to n respective directional images to remove non-uniform illumination. The output uniformly illuminated directional images $I_i$ are enhanced according to EQUATION 7 and EQUATION 8. Finally, all enhanced directional images are re-combined to yield the final filtered image F as in EQUATION 9.

FIG. 7 shows the results of an synthetic image which was processed by the three filter models. The synthetic image in FIG. 7A is designed to contain vessels of different sizes and junctions of different types. It is possible to see that the Frangi (FIG. 7B) and Shikata (FIG. 7C) filters unexpectedly suppress junctions while our proposed approach (FIG. 7D) does not. The suppressed junctions make vessels discontinuous.

It is the use of directional image decomposition that makes the proposed model work. Normally, a vessel has one principal direction, which is mathematically indicated by a small ratio between the smaller and larger Hessian eigenvalue.

Meanwhile, at a junction, where a vessel branches off, there are more than two principal directions, and thus the ratio of two eigenvalues is no longer small. As a result, the conventional enhancement filters (e.g., the Frangi and Shikata filters) consider those points as noise and then suppress them. Our proposed approach, on the other hand, decomposes the input image to various directional images, each of which contains vessels with similar orientations. Consequently, junctions do not exist in directional images and so are not suppressed during the filtering process. After that, due to the re-combination of enhanced directional images, junctions are re-constructed at those points which have vessel values in more than two directional images.

Figure 8A:
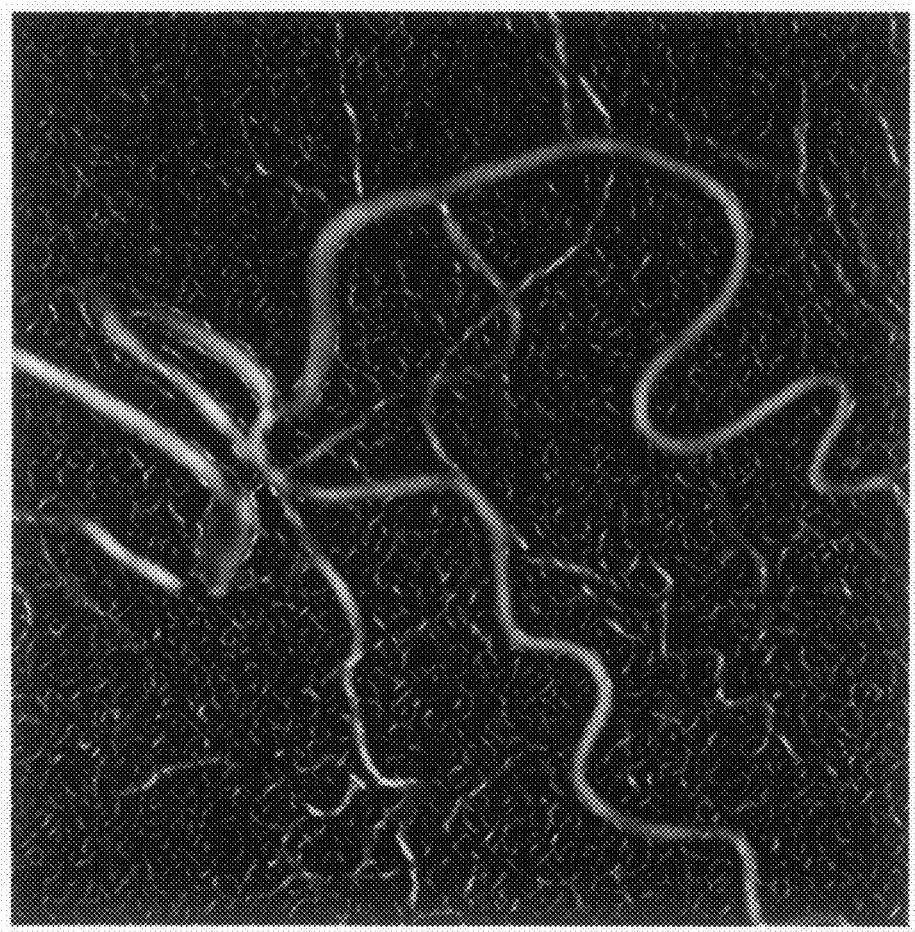
FIGS. 8A, 8B, and 8C are showing enhancement results of the Frangi filter, the Shikata filter and the present invention for the input image shown in FIG. 1.
Figure 8B:
Figure 8C:
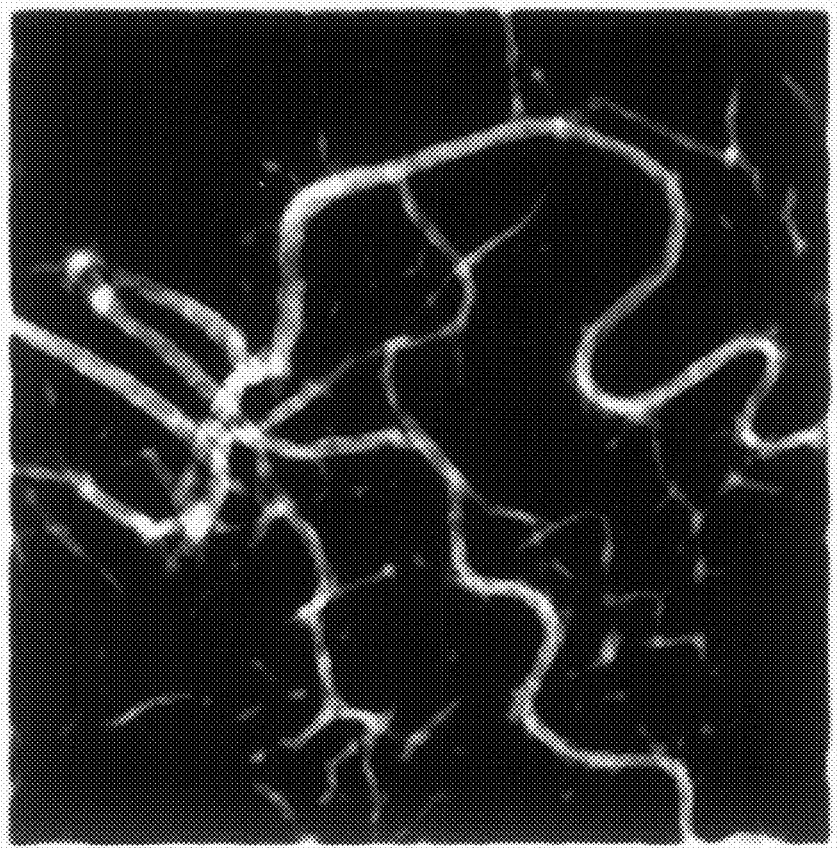

FIGS. 8A, 8B, and 8C respectively show enhancement results of Frangi filter, Shikata filter and our present invention for the input images shown in FIG. 1. As can be observed, Frangi filter gives good results with large vessels but fails to detect small ones while Shikata model is able to enhance small vessels but unfortunately enhances background noise also. Conversely, our proposed filter can enhance small vessels with more continuous appearances.

What is claimed is:

1. A method for enhancing blood vessels in an angiography image, the method comprising the steps of:
    decomposing the angiography image into n directional images $T_i$, i=1 . . . n, using DDFB;
    removing non-uniform illumination by employing n distinct homomorphic filters, each of which corresponds to one of the n directional images;
    enhancing n directional images using n vessel enhancement filters; and
    re-combining n enhanced directional images.

2. The method as claimed in claim 1, wherein the number n of directional images is $2^k$ (k is a positive integer).

3. The method as claimed in claim 1, wherein said decomposing the angiography image comprises steps of:
    a) filtering the angiography image with $H_{00}(\omega_1, \omega_2)$ and $H_{11}(\omega_1, \omega_2)$, each having hourglass-shaped like passbands;
    b) filtering each filtered output of step (a) with $H_{00}(Q^T(\omega_1, \omega_2))$ and $H_{11}(Q^T(\omega_1, \omega_2))$, where T represents transpose and Q is Quincunx downsampling matrix; and
    c) filtering each filtered output of step (b) with $H_{00}(R_i Q^T Q^T (\omega_1, \omega_2))$ and $H_{11}(R_i Q^T Q^T (\omega_1, \omega_2))$, where i=1, 2, 3, 4, and $R_i$, are $$R_1 = \begin{pmatrix} 1 & 1 \\ 0 & 1 \end{pmatrix} R_2 = \begin{pmatrix} 1 & -1 \\ 0 & 1 \end{pmatrix}$$
$$R_3 = \begin{pmatrix} 1 & 0 \\ 1 & 1 \end{pmatrix} R_4 = \begin{pmatrix} 1 & 0 \\ -1 & 1 \end{pmatrix}.$$

4. The method as claimed in claim 3, wherein $R_i$, and Q are respectively resampling and downsampling matrices.

5. The method as claimed in claim 1, wherein output of the vessel enhancement filter applied on a directional image $T_i$, i=1 . . . n, is $$\Phi(p) = \max_{\sigma \in S} \phi_\sigma(p),$$

where p is coordinate (x',y') in a coordinate system Ox'y', S is a range, and σ is various scale.

6. The method as claimed in claim 5, wherein the coordinate system Ox'y' is obtained by rotating Oxy, where Oxy is a coordinate system originated at the top left corner and ordered from top to bottom and left to right of the directional image $T_i$.

7. The method as claimed in claim 5, wherein the vessel enhancement filer at a certain scale σ is $$\phi_\sigma(p) = \eta(PC_2)\exp\left(-\frac{R^2}{2\beta^2}\right)\left[1 - \exp\left(-\frac{C^2}{2\gamma^2}\right)\right],$$

where $PC_1$ and $PC_2$ are the diagonal values of Hessian matrix H' in the coordinate system Ox'y', $R=PC_1/PC_2$, $C=\sqrt{PC_1^2 + PC_2^2}$, β and γ are adjusting constants, and $$\eta(z) = \begin{cases} 0 & \text{if } z \geq 0; \\ 1 & \text{if } z < 0. \end{cases}$$

8. The method as claimed in claim 7, wherein the Hessian matrix is $$H' = \begin{bmatrix} \frac{\partial^2 T_i}{\partial x'^2} & \frac{\partial^2 T_i}{\partial x' y'} \\ \frac{\partial^2 T_i}{\partial x' y'} & \frac{\partial^2 T_i}{\partial y'^2} \end{bmatrix}, \text{ where}$$

$$\frac{\partial^2 T_i}{\partial x'^2} = \frac{\partial^2 T_i}{\partial x^2}\cos^2\theta_i + \frac{\partial^2 T_i}{\partial x \partial y}\sin(2\theta_i) + \frac{\partial^2 T_i}{\partial y^2}\sin^2\theta_i,$$

$$\frac{\partial^2 T_i}{\partial y'^2} = \frac{\partial^2 T_i}{\partial x^2}\sin^2\theta_i - \frac{\partial^2 T_i}{\partial x \partial y}\sin(2\theta_i) + \frac{\partial^2 T_i}{\partial y^2}\cos^2\theta_i, \text{ and}$$

$$\frac{\partial^2 T_i}{\partial x' \partial y'} = -\frac{1}{2}\frac{\partial^2 T_i}{\partial x^2}\sin(2\theta_i) + \frac{\partial^2 T_i}{\partial x \partial y}\cos(2\theta_i) + \frac{1}{2}\frac{\partial^2 T_i}{\partial y^2}\sin(2\theta_i).$$

* * * * *